United States Patent
Wong et al.

(12)

(10) Patent No.: US 6,353,095 B1
(45) Date of Patent: Mar. 5, 2002

(54) KETOALDONIC ACIDS HAVING FORMED STEREOGENIC CENTERS OF R CONFIGURATION: METHODS AND COMPOSITIONS

(75) Inventors: Chi-Huey Wong, Rancho Santa Fe; Chun-Hung Lin, San Diego, both of CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 07/946,546

(22) Filed: Sep. 17, 1992

Related U.S. Application Data

(63) Continuation-in-part of application No. 07/763,359, filed on Sep. 20, 1991, now Pat. No. 5,162,513.
(51) Int. Cl.$^7$ .............................. C07H 5/04; C07H 1/00
(52) U.S. Cl. .................... 536/1.11; 536/18.7; 536/18.5; 536/53; 536/55; 514/23; 514/8; 424/88; 424/92; 435/137
(58) Field of Search ................................. 536/1.1, 18.7, 536/53, 55, 18.5; 514/23, 8, 25; 424/88, 92; 435/7.35, 7.9, 137

(56) References Cited

U.S. PATENT DOCUMENTS 4,613,589 A * 9/1986 Rosenbrook et al. ......... 536/1.1
4,613,590 A * 9/1986 Rosenbrook et al. ......... 514/23
4,870,053 A * 9/1989 Zalisz et al. .................... 514/8

OTHER PUBLICATIONS

Roberts et al., *Basic Principles of Organic Chemistry*, W. A. Benjamin, Inc., New York, Amsterdam, 1965, pp. 616–622.
Cram et al., *Organic Chemistry*, McGraw–Hill Book Company, Inc., New York, 1959, pp. 112–115, 138–139.
White et al., *Principles of Chemistry*, McGraw–Hill Book Company, New York, 1978, pp. 12–21.
Wallace et al., *Biology The Science Of Life*, Scott, Foresman and Company, Glenview, Illinois, 1986, pp. 50–55.
Morrison et al., *Organic Chemistry*, Allyn and Bacon, Inc., Boston, 1966, pp. 1001–1014.
Aldrich Catalogue, Milwaukee, p. 890.
*The Merck Index*, Tenth Edition, Merck & Co., Inc., Rathway, New Jersey, 1983, pp. 4459 and 4460.
Paulsen et al, Liebigs Ann. Chem. (1988), p 277–279.*
Schreiner et al, Liebigs Ann. Chem 1990, 581–586.*
Schreil et al, Liebigs Ann. Chem. 1990, 1111–1114.*

* cited by examiner

*Primary Examiner*—Louise N. Leary
(74) *Attorney, Agent, or Firm*—Welsh & Katz, Ltd.

(57) ABSTRACT

The present invention provides a ketoaldonic acid such as an octulosonic or nonulosonic acid having a formed stereogenic center of R configuration, as well as methods of synthesizing the same.

10 Claims, No Drawings

KETOALDONIC ACIDS HAVING FORMED STEREOGENIC CENTERS OF R CONFIGURATION: METHODS AND COMPOSITIONS

CROSS-REFERENCE TO RELATED APPLICATION

This is a continuation-in-part of application Ser. No. 07/763,359, filed Sep. 20, 1991 now U.S. Pat. No. 5,162,513.

This invention was made with government support under Contract No. GM 44154 awarded by the National Institutes of Health. The government has certain rights in the invention.

TECHNICAL FIELD OF THE INVENTION

The present invention relates to ketoaldonic acids having formed stereogenic centers of R configuration, particularly octulosonic and nonulosonic acids, and methods for synthesizing such sugars using sialic acid aldolase.

BACKGROUND OF THE INVENTION

A major synthetic value of enzyme catalysis is its usually predictable stereoselectivity. See, e.g., Whitesides et al., *Angew. Chem. Int. Ed. Engl.,* 24:617 (1985); Jones, *Tetrahedron,* 42:3351 (1986); Yamada et al., *Angew. Chem. Int. Ed. Engl.,* 27:622 (1988); Wong, C-H., *Science,* 244:1145 (1989); Ohno et al., *Org. React.,* 37:1 (1989); Chen et al., *Angew. Chem. Int. Ed. Engl.,* 28:695 (1989).

A change of stereoselectivity, however, may occur, though very unusual, with different substrate structures, temperatures or solvents. See. e.g., Mohr et al., *Helv. Chim. Acta,* 66:2501 (1983); Sabbioni et al., *J. Chem. Soc. Chem. Commun.,* 236 (1984); Ohno et al., *J. Am. Chem. Soc.,* 103:2405 (1983); Wang et al., *J. Org. Chem.,* 53:3127 (1988); Lalonde et al., *J. Am. Chem. Soc.,* 103:2405 (1981); Wang et al., *J. Org. Chem.,* 53:2323 (1988); Pham et al., *J. Am. Chem. Soc.,* 111:1935 (1989); Keinan et al., *J. Am. Chem. Soc.,* 108:162 (1986); Sakurai et al., *J. Am. Chem. Soc.,* 110:7236 (1988); Fitzpatrick et al., *J. Am. Chem. Soc.,* 113:3166 (1991). These selectivity changes are often not very significant, with some exceptions where the enantioselectivity is inverted.

In the case of enzymatic aldol reactions, the diastereofacial selectivity for the aldehyde component is often consistent and completely controlled by the enzyme as documented by numerous reactions catalyzed by fructose-1,6-diphosphate (FDP) aldolase or N-acetylneuraminic acid (or sialic acid) aldolase (EC 4.1.3.3). In most cases, the "D" isomer of an α-substituted aldehyde reacts faster than the "L" isomer, both with si-facial selectivity. The Cram-Felkin mode of attack on the "D" aldehyde is therefore proposed for the transition state of the FDP aldolase reaction and the anti-Cram-Felkin mode for the sialic acid aldolase reaction. See. e.g., Toone et al., *Tetrahedron,* 45:5365 (1989); Bednarski et al., *J. Am. Chem. Soc.,* 111:627 (1989); Straub et al., *J. Org. Chem.,* 55:3926 (1990); Durrwachter et al., *J. Org. Chem.,* 53:4175 (1988); von der Osten et al., *J. Am. Chem. Soc.,* 111:3924 (1989); Kajimoto et al., *J. Am. Chem. Soc.,* 113:6187 (1991); Auge et al., *New J. Chem.,* 12:733 (1988).

Because of the stereoselectivity of enzymes such as aldolases that participate in the metabolism of carbohydrates, it is extremely difficult to design and make new carbohydrates that can be used to study carbohydrate metabolism. There is a need for such synthetic compounds for use as experimental tools in elucidating the molecular character of the numerous and varied pathways involved in carbohydrate anabolism and catabolism.

Of particular relevance to the present invention is the sugar, N-acetylneuraminic acid (NeuAc) or sialic acid. NeuAc is an integral component of most cells and is believed to play a major role in imparting electrical charge characteristics to such cells. Further, NeuAc-like compounds such as the eight and nine-carbon sugar moieties KDO and KDN are major constituents of non-mammalian tissues.

N-Acetylneuraminic Acid (NeuAc) aldolase, also commonly referred to as sialic acid aldolase is a type I aldolase known to form an enamine intermediate with pyruvate, which reversibly reacts with the second substrate N-acetylmannosamine to give NeuAc. See, e.g., Deijl et al., *Biochem. Biophys. Res. Commun.,* 111:668 (1983); and Shukla et al., *Anal. Biochem.,* 158:158 (1986).

NeuAc aldolase is known to accept many aldoses as acceptor substrates. In all previously known aldol condensation reactions with such acceptor substrates, the eneamine intermediate approaches the si face of the incoming aldehyde substrate to form a new stereogenic center of S configuration. Anti-Cram-Felkin attack is generally observed for good chiral aldehyde substrates and Cram-Felkin attack is observed for weak substrates. In both cases, a si-facial selectivity was observed. See. e.g., Auge et al., *New J. Chem.,* 12:733 (1988); and Auge et al., *Tetrahedron,* 46:201 (1990).

Based on such current knowledge concerning aldolase stereoselectivity, therefore, NeuAc aldolase is considered to be useful only for the production of D-sugars having S configuration. As is disclosed hereinafter, NeuAc aldolase has now unexpectedly been found to be capable of the production of certain ketoaldonic acids having a formed stereogenic center of R configuration.

BRIEF SUMMARY OF THE INVENTION

In one aspect, the present invention contemplates ketoaldonic acids, and particularly octulosonic or nonulosonic acids, having a formed stereogenic center of R configuration. A contemplated ketoaldonic acid is a sialic acid aldolase-catalyzed condensate of pyruvate and an acceptor substrate aldose for that enzyme. The ketoaldonic acid contains a stereogenic center of the R configuration other than present in the acceptor substrate aldose. Exemplary acceptor substrate aldoses include D-gulose and a five or six carbon L-configured acceptor substrate aldose other than L-arabinose, which form an octulosonic or nonulosonic acid. In another aspect, the present invention contemplates a compound having the Formulae I-VIII, below, in which compounds of Formulae V-VIII, are particularly preferred.

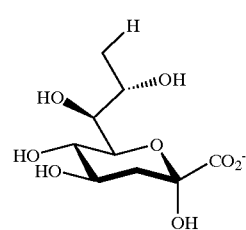

I

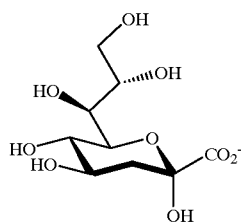
II

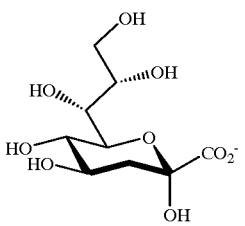
III

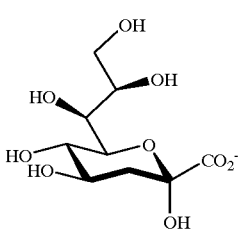
IV

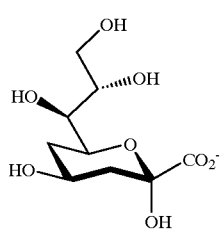
V

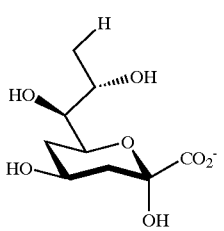
VI

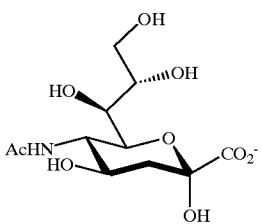
VII

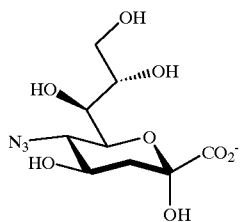
VIII

Although L-arabinose forms an octulosonic acid with a new S rather than R stereogenic center in the above sialic acid aldolase-catalyzed condensation with pyruvate, the product of that reaction, 3-deoxy-L-manno-octulosonic acid (L-KDO), a compound of Formula IX, below is new and unexpectedly produced.

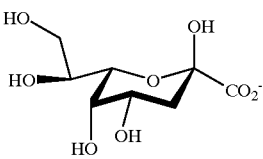
IX

One aspect contemplates a process for preparing a ketoaldonic acid having a new stereogenic center of the R configuration, relative to the aldose starting material. This process comprises the steps of:

(a) admixing in an aqueous solvent (i) pyruvate (typically in excess), (ii) a catalytic amount of sialic acid aldolase and (iii) an acceptor substrate aldose for that enzyme, such as D-gulose or a five or six carbon L-configured acceptor substrate aldose other than L-arabinose, to form a reaction mixture; and (b) maintaining the reaction mixture for a time period and under biological reaction conditions sufficient for condensation of the pyruvate with the acceptor substrate aldose and the formation of a ketoaldonic acid product.

That product is preferably recovered. Use of D-gulose or a five or six carbon L-configured acceptor substrate aldose forms an octulosonic or nonulosonic acid.

In another process aspect, the present invention contemplates a process for synthesizing a compound of Formulae I-VIII comprising the steps of:

(a) admixing pyruvate (typically in excess), in the presence of a catalytic amount of sialic acid (NeuAc) aldolase, with an acceptor substrate L-rhamnose, L-mannose, L-talose, D-gulose, 2-deoxy-L-glucose, 2-deoxy-L-rhamnose, N-acetyl-L-mannosamine or 2-azido-2-deoxy-L-mannose, respectively, (the latter four aldoses being preferred) to form a reaction mixture; and (b) maintaining the reaction mixture for a time period and under biological reaction conditions sufficient for condensation of the pyruvate with the acceptor substrate and formation of a compound of Formulae I-VIII, above.

In a preferred embodiment, the synthetic method further comprises recovering the synthesized compound of Formulae I–VIII.

In another embodiment, the invention contemplates an enhanced process for synthesizing any ketoaldonic acid such as an octulosonic or nonulosonic acid like sialic acid. In accordance with this process, an excess of pyruvate, e.g. about 2 to about 10 fold excess, and an acceptor substrate aldose for sialic acid aldolase (EC 4.1.3.3) and a catalytic amount of that aldolase are admixed in an aqueous solvent to form a reaction mixture. That reaction mixture is maintained for a time period and under biological reaction conditions sufficient for the condensation of the pyruvate with the acceptor substrate aldose to form a ketoaldonic acid such as an octulosonic or nonulosonic acid where a five or six carbon acceptor substrate aldose is used.

The enzyme pyruvate decarboxylase is then added and the resulting composition is maintained as above until the excess pryuvate is decomposed. This addition preferably occurs after denaturation of sialic acid aldolase as by acidification. The added pyruvate decarboyxlase can be added as the purified enzyme or as whole acid-free baker's yeast cells. The ketoaldonic acid is thereafter recovered by standard procedures that include a separation from the yeast cells, where used.

DETAILED DESCRIPTION OF THE INVENTION

A. Compounds

The present invention contemplates a ketoaldonic acid such as octulosonic and nonulosonic acids. A contemplated ketoaldonic acid is a sialic acid aldolase-catalyzed condensate of pyruvate and an acceptor substrate aldose for that enzyme. The ketoaldonic acid contains a stereogenic center of the R configuration other than present in the acceptor substrate aldose. Exemplary acceptor substrate aldoses include D-gulose and a five or six carbon L-configured acceptor substrate aldose other than L-arabinose, which form an octulosonic or nonulosonic acid. Exemplary octulosonic and nonulosonic acid compounds have the Formulae I, II, III, IV, V, VI, VII or VIII, below, with compounds of Formulae V–VIII being preferred.

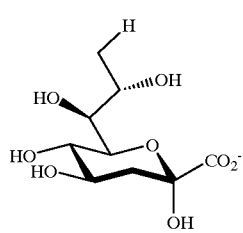

I

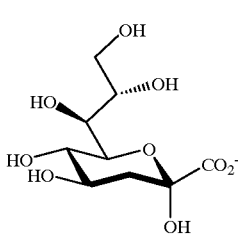

II

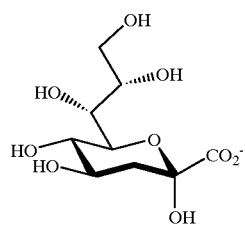

III

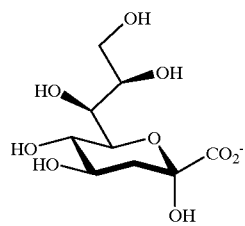

IV

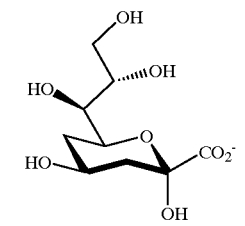

V

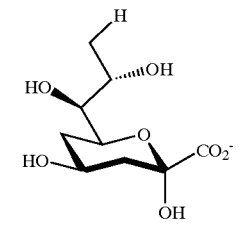

VI

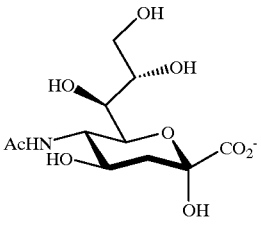

VII

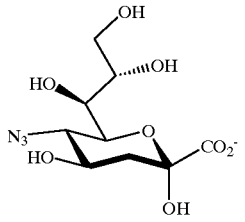

VIII

Formula I defines 3,9-dideoxy-L-glycero-L-galactononulosonic acid. Given that 3,9-dideoxy-D-glycero-D-galactononulosonic acid defines D-9-deoxy KDN, the compound of Formula I can also be referred to as L-9-deoxy KDN.

Formula II defines 3-deoxy-L-glycero-L-galactononulosonic acid, which can also be referred to as L-KDN.

The compounds of Formulae I-VIII have a $^5C_2$ conformation as evidenced by the adjacent transaxial coupling of protons at the carbon atoms at positions 3, 4 and 5. Further, the compounds of Formulae I-VIII have a formed stereogenic center of R configuration.

The compounds of Formulae I-VIII synthesized in accordance with the method described herein have a formed stereogenic center of R configuration that is created via the re attack of pyruvate on the acceptor substrate. This re attack and resulting R configuration are surprising and unexpected in view of the published literature. In all previously known aldol condensation reactions using NeuAc aldolase (EC 4.1.3.3), the attack is on the si face of the acceptor substrate and the resulting condensation product has a formed stereogenic center of S configuration. See. e.g., Auge et al., *New J. Chem.*, 12:733 (1988); Auge et al., *Tetrahedron*, 46:201 (1990); and Kim et al., *J. Am. Chem. Soc.*, 110:6481 (1988).

Thus, where N-acetyl D-mannosamine (D-ManNAc), D-mannose (Man), 4-deoxy-D-Man, 2-deoxy-2-phenyl-D-Man, 6-O-Ac-D-ManNAc, 6-O-Ac-D-Man, 2-deoxy-D-glucose, 6-deoxy-6-$N_3$-D-ManNAc, 6-deoxy-6-F-D-ManNAc, 4,6-dideoxy-4,6-$F_2$-D-talose, D-glucose (D-Glc), D-altrose, 2-deoxy-D-galactose, D-glucosamine (GlcNAc), D-lyxose, D-talose, D-arabinose, L-arabinose or 2-deoxyribose was reacted with pyruvate and a catalytic amount of NeuAc aldolase, the resulting condensation products were all found to have formed stereogenic centers of S configuration resulting from a si facial attack. Wong, C-H., *Microbial Aldolases* in *Enzymes in Carbohydrate Synthesis* ed. by Bednarski and Simon, American Chemical Society, ACS Symposium Series No. 466 (1991).

The re attack and resulting R configuration where L-rhamnose, L-mannose, L-talose, D-gulose, 2-deoxy-L-glucose, 2-deoxy-L-rhamnose, N-acetyl-L-mannosamine and 2-azido-2-deoxy-L-mannose were used as the acceptor substrate are even more surprising and unexpected because such reversal of stereoselectivity was not observed with all L-isomeric acceptor substrates. Where L-glucose or L-fucose were reacted with pyruvate in the presence of NeuAc aldolase, no aldol condensation product was formed. Wong, C. -H., *Microbial Aldolases* in *Enzymes in Carbohydrate Synthesis* ed. by Bednarski and Simon, American Chemical Society, ACS Symposium Series No. 466 (1991).

Another new and useful compound that has a newly formed S rather than R stereogenic center is L-KDO, a compound of Formula IX, below.

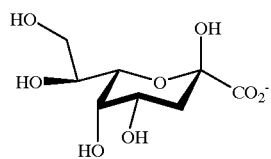

IX

B. Synthetic Process

Another aspect of the present invention contemplates an aldol condensation process of synthesizing a ketoaldonic acid such as an octulosonic or nonulosonic acid that are exemplified by the compounds of Formulae I-VIII. The formed ketoaldonic acid such as an octulosonic or nonulosonic acid contains a new stereogenic center relative to the starting reactants; i.e., not present in the acceptor substrate aldose reactant, and that new stereogenic center has the R configuration. This process comprises the steps of admixing in an aqueous solvent pyruvate (typically in excess), a catalytic amount of sialic acid aldolase and an acceptor substrate aldose for that enzyme such as D-gulose or a five or six carbon L-configured acceptor substrate aldose other than L-arabinose to form a reaction mixture. The reaction mixture is maintained for a time period and under biological reaction conditions sufficient to condense the pyruvate and acceptor substrate aldose and form a desired octulosonic or nonulosonic acid.

In accordance with another aldol condensation process, pyruvate (typically in excess) is admixed in an aqueous solvent in the presence of a catalytic amount of sialic acid (NeuAc) aldolase, with an acceptor substrate as named before to form a reaction mixture. The reaction mixture is maintained for a time period and under biological reaction conditions sufficient to condense the pyruvate and acceptor substrate and form a compound of Formulae I, II, III, IV, V, VI, VII or VIII, as appropriate to the before-noted acceptor substrate, with formation of a compound of Formulae V-VIII being preferred.

The structure of the acceptor substrate dictates the structure of the synthesized aldol condensation product. Where the acceptor substrate is L-rhamnose, the compound of Formula I is synthesized. Where the acceptor substrate is L-mannose, the compound of Formula II is synthesized. Where the acceptor substrate is L-talose, the compound of Formula III is synthesized. Where the acceptor substrate is D-gulose, the compound of Formula IV is synthesized. With 2-deoxy-L-glucose as acceptor substrate, the compound of Formula V is synthesized in a 5:1 ratio to the si face adduct (axial 3-hydroxy group). 2-Deoxy-L-rhamnose is the acceptor substrate for the compound of Formula VI. Where N-acetyl-L-mannosamine is the acceptor substrate, a compound of Formula VII is synthesized. Where 2-azido-2-deoxy-L-mannose is the acceptor substrate, a compound of Formula VIII is formed in a 4.5:1 ratio to the si face adduct (axial 3-hydroxy group).

Pyruvate is readily available from commercial sources (Sigma Chemical Co., St. Louis, Mo.). A preferred formulation of pyruvate is sodium pyruvate. Pyruvate is typically used in an amount in excess of the one mole required for the reaction to drive the reaction to completion. A 2- to about 10-fold excess is usually used.

L-Mannose, L-rhamnose, L-talose and D-gulose are also available from Sigma Chemical Co. 2-Deoxy-L-glucose (Compound 5), 2-deoxy-L-rhamnose (Compound 6), N-acetyl-L-mannosamine (Compound 11) and 2-azido-2-deoxy-L-mannose (Compound 9a) are synthesized as discussed hereinafter.

Highly stable NeuAc aldolase in a free or immobilized form is readily available. See. e.g., Auge et al., *New J. Chem.*, 12:733 (1988); Auge et al., *Tetrahedron*, 46:201 (1990); and Kim et al., *J. Am. Chem. Soc.*, 110:6481 (1988).

As used herein, the phrase "catalytic amount" means that amount of NeuAc aldolase at least sufficient to catalyze, in a non-rate limiting manner, the condensation of pyruvate and acceptor substrate to product. More than a catalytic amount can be used.

The catalytic amount of NeuAc aldolase varies according to the specific activity of NeuAc aldolase The reaction time varies with the temperature and the activity of the NeuAc aldolase. Where the NeuAc aldolase has an activity of about 10 Units, the temperature is about 37° C., and the concentration of acceptor substrate is about 1 mM, the reaction time is about 48 hours (See Examples 1A and 1B hereafter).

The synthetic method of the present invention can further include recovering a synthesized (formed) ketoaldonic acid such as a compound of Formulae I-VIII. Recovering comprises isolating the synthesized compound from the reaction mixture. Means for isolating a synthesized ketoaldonic acid such as a compound of Formulae I-VIII include gel filtration, column chromatography, paper chromatography, affinity chromatography, extraction, crystallization, precipitation and the like.

In a preferred embodiment, isolation is accomplished by applying a reaction mixture containing about 1 mM acceptor substrate to an anion exchange chromatography column of Dowex® 1×8–100 (HCOO$^-$ or HCO$_3^-$ form; 30×2 or 20×2.5 cm) and eluting a compound of Formulae I-VIII with formic acid (0.2M) or bicarbonate (0→0.2M), respectively. Product-containing fractions are then pooled, freeze-dried and deionized with Dowex® W-X8 [H$^+$], and freeze dried again. The pure compounds are finally obtained by bio-gel chromatography. Where such an embodiment is used for isolation, a compound of Formula I can typically be recovered with a yield of about 80 percent (See Example 1A).

The reaction rate of the method of the present invention is within a factor of about 10 of the reaction rate of NeuAc aldolase-catalyzed condensation of pyruvate with acceptor substrates having an enantiomeric configuration (i.e., D-rhamnose, D-mannose, D-talose, L-gulose, 2-deoxy-D-glucose, 2-deoxy-D-(Units/mg), the concentration of acceptor substrate as well as biological reaction conditions such as temperature, time and pH value. Means for determining the catalytic amount of NeuAc aldolase under preselected substrate concentrations and biological reaction conditions are well known to those of skill in the art. Typical amounts range from about 5 to about 20 Units (U) per millimole (mmol) of acceptor substrate, with about 10 to about 15 U/mmol typically being used.

Each ingredient is admixed with each of the other ingredients in a suitable aqueous solvent to form a reaction mixture. The reaction mixture is maintained under biological reaction conditions (temperature, pH, solvent osmolality, ionic composition and ambient pressure) for a period of time sufficient to condense the substrate acceptor and pyruvate to form a compound of Formula I, II, III, IV, V, VI, VII or VIII. A compound of Formula IX can be similarly prepared using L-arabinose as the acceptor substrate aldol.

Temperature can range from about 15° C. to about 40° C. Preferably, temperature is from about 20° C. to about 40° C. and, more preferably from about 25° C. to about 37° C.

The pH value of the solvent and for maintenance can range from about 6.0 to about 11.0. Preferably, the pH value is from about 6.0 to about 8.5 and, more preferably from about 7.0 to about 7.5. The pH value is maintained by buffers in the aqueous solvent. A preferred buffer is potassium phosphate.

The aqueous solvent preferably further comprises an anti-oxidant. A preferred anti-oxidant is a sulfur-containing reducing agent such as a mercaptan (thiol). Exemplary mercaptans are mercaptoethanol and dithiothreitol. rhamnose, N-acetyl-D-mannosamine or 2-azido-2-deoxy-D-mannose). The substantial similarity of the reaction rates with D- and L-configured acceptor substrates is surprising and unexpected. With aldolases other than NeuAc aldolase (i.e., fructose-1,6-diphosphate aldolase), the reaction rate is markedly faster with D-configured acceptor substrates than with L-configured acceptor substrates. See. e.g., Toone et al., *Tetrahedron*, 45:5365 (1989); Bednarski et al., *J. Am. Chem. Soc.*, 111:627 (1989); Straub et al., *J. Org. Chem.*, 55:3926 (1990); Durrwachter et al., *J. Org. Chem.*, 53:4175 (1988); von der Osten et al., *J. Am. Chem. Soc.*, 111:3924 (1989); Kajimoto et al., *J. Am. Chem. Soc.*, 113:6187 (1991).

An improved process for the synthesis of a ketoaldonic acid such as an octulosonic or nonulosonic acid is contemplated in another embodiment of the invention. This improved process is useful regardless of which enantiomer is prepared; i.e., for any ketoaldonic acid.

Here, an excess of pyruvate, typically about a 2- to about 10-fold excess, is admixed in an aqueous solvent with a catalytic amount of sialic acid aldolase and an acceptor substrate for that enzyme to form a reaction mixture. Specific exemplary D- and L-acceptor substrates are noted before. The reaction mixture is maintained for a time period and under biological reaction conditions sufficient to condense the pyruvate and acceptor substrate to form an octulosonic or nonulosonic acid.

The reaction conditions utilized in this embodiment are as discussed previously. Additional aldose acceptor substrates for sialic acid aldolase are discussed before and are discussed in Wong, C-H., *Microbial aldolases in Enzymes in Carbohydrate*

1. 3-Deoxy-D-glycero-L-altro-nonulosonic acid (Compound of Formula III)

$[a]^{25}_D$+32.1° (c 0.41, H$_2$O); $^1$H NMR (D$_2$O, HOD=4.80 ppm) δ3.98 (1H, ddd, J$_{8-9a}$=7.0 Hz, J$_{8-9a}$=5 Hz, J$_{8-7}$=2.5 Hz, H-8), 3.95 (1H, ddd, J$_{4-3ax}$=12.5 Hz, J$_{4-5}$=9.0 Hz, J$_{4-3eq}$=5.0 Hz, H-4), 3.93 (1H, dd, J$_{7-6}$=3.5 Hz, J$_{7-8}$=2.5 Hz, H-7), 3.85 (1H, dd, J$_{6-5}$=9.5 Hz, J$_{6-7}$3.5 Hz, H-6), 3.69 (1H, dd, J$_{9b-9a}$=11.5 Hz, J$_{9b-8}$=5.0 Hz, H-9b), 3.65 (1H, dd, J$_{9a-9b}$=11.5 Hz, J$_{9a-8}$=7 Hz, H-9a), 3.56 (1H, t, J$_{5-6}$=J$_{5-4}$=9.5 Hz, H-5), 2.21 (1H, dd, J$_{3eq-3ax}$=12.5 Hz, H-3ax). $^{13}$C NMR (D$_2$O+CD$_3$CN) δ176.9, 96.7, 74.4, 96.7, 74.4, 72.2, 71.6, 71.1, 69.4, 63.2, 39.3 HRMS (FAB) calcd for C$_9$H$_{16}$O$_9$Na (M+Na$^+$) 291.0692, found 291.0698.

2. 3,5-Dideoxy-L-glycero-L-galacto-nonulosonic acid (Compound of Formula V)

$[a]^{25}_D$+35.80° (c 0.27, H$_2$O); $^1$H NMR (D$_2$O) δ4.13 (1H, m, H-4) 4.10 (1H, dt, J$_{6-5ax}$=12.0 Hz, J$_{6-5eq}$=J$_{6-7}$=2.0 Hz, H-6), 3.77 (1H, dd, J$_{9a-9b}$=12.0 Hz, J$_{9a-8}$=3.0 Hz, H-9a), 3.72 (1H, ddd, J$_{8-7}$=9.0 Hz, J$_{8-9a}$=3.0 Hz, H-8), 3.56 (1H, dd, J$_{9b-9a}$=12.0 Hz, J$_{9b-8}$=6.5 Hz, H-9b), 3.41 (1H, dd, J$_{7-8}$=3.5 Hz, J$_{7-6}$=1.5 Hz, H-7), 2.03 (1H, ddd, J$_{3eq-3ax}$=12.5 Hz, J$_{3eq-4}$=4.5 Hz, J$_{3eq-5eq}$=1.5 Hz, H-3eq), 1.82 (1H, b dt, J$_{5eq-5ax}$=12.0 Hz, J$_{5eq-6}$=J$_{5eq-4}$=2.0 Hz, H-5eq), 1.56 (1H, dt, J$_{5ax-4}$=11.5 Hz, J$_{5ax-6}$=J$_{5ax-5eq}$=12.0 Hz, H-5ax) 1.49 (1H, t, J$_{3ax-3eq}$=J$_{3ax-4}$=12.0 Hz, H-3ax). $^{13}$C NMR (D$_2$O+CD$_3$CN) δ177.8, 97.4, 73.2, 71.3, 68.6, 64.5, 63.5, 40.3, 35.7. HRMS (FAB) calcd for C$_9$H$_{16}$O$_8$Na (M+Na$^+$) 275.0743, found 275.0751.

3. 3,5,9-Trideoxy-L-glycero-L-galacto-nonulosonic acid (Compound of Formula VI)

$[a]^{25}_D$+22.1° (c 0.19, H$_2$O) $^1$H NMR (D$_2$O) δ4.12 (1H, ddt, J$_{4-3eq}$=5.0 Hz, J$_{4-5eq}$=2.5 Hz, J$_{4-3ax}$=J$_{4-5ax}$=12.0 Hz, H-4), 4.07 (1H, dt, J$_{6-5ax}$=12.0 Hz, J$_{6-5eq}$=J$_{6-7}$=2.5 Hz, H-6), *Synthesis*, ed. by Bednarski and Simon, American Chemical Society, ACS Symposium Series No. 466 (1991). Non-substrates are also discussed. Whether an aldose is an acceptor substrate for this enzyme can be readily ascertained by admixture of excess pyruvate, the enzyme and potential acceptor substrate aldose as discussed herein, followed by maintenance as discussed herein, e.g. 2–3 days. Analysis of the reaction mixture as by thin layer chromatography indicates whether an octulosonic or nonulosonic acid has been formed.

After the ketoaldonic acid has formed, a catalytic amount of pyruvate decarboxylase is admixed to the aqueous solvent medium and the resulting admixture is maintained as before, but using a pH value of about 5.5 to about 6.5, until the pyruvate has decomposed. This step is utilized because it has been found that the excess pyruvate utilized in the condensation reaction interferes with recovery of the ketoaldonic acid product. Thus, for example, in previously reported procedures for the isolation of enzymatically produced sialic acid [Kim et al., *J. Am. Chem. Soc.*, 110:6481 (1988) and Liu et al., *J. Am. Chem. Soc.*, 114:3901 (1992)] a repetitive extraction of pyruvic acid with ethyl acetate under acidic conditions was used. Under those conditions, the pyruvate exists mainly as the hydrated form in the aqueous phase where its presence makes isolation of sialic acid difficult.

The pyruvate decarboxylase (EC 4.1.1.1) is preferably admixed after denaturation of the sialic acid aldolase. That enzyme is conveniently denatured by adjusting the solution pH value to about 2 and maintaining the pH value for about one hour.

The pyruvate decarboxylase can be provided as a purified enzyme as is available from Sigma Chemical Co. at $80.00 per 100 Units. That enzyme can also be provided by culturing baker's yeast cells. Baker's yeast cells are much less costly, e.g. $16.00 per 500 g from Sigma. The baker's yeast cells must be acid-free, which can be accomplished by washing the cells as described hereinafter.

After the excess pyruvate has been decomposed, the ketoaldonic acid such as octulosonic or nonulosonic acid is recovered by usual techniques such as by ion exchange chromatography or crystallization. Where baker's yeast cells are used as the source of the pyruvate decarboxylase, the cells are removed as by centrifugation prior to use of ion exchange or other techniques. Exemplary procedures for recovery of the octulosonic or nonulosonic acids are illustrated hereinafter.

The following Examples illustrate particular embodiments of the present invention and are not limiting of the specification and claims in any way.

EXAMPLE 1

Syntheses

A. Synthesis of 3,9-Dideoxy-L-glycero-L-galactononulosonic acid (L-9-deoxy KDN) (Compound of Formula I)

A 0.1 M solution of L-rhamnose (1 mmol) in a 0.05 M potassium phosphate buffer, pH 7.2, containing 0.01 M dithiothreitol, sodium pyruvate (3 equivalent) and 10 U of NeuAc aldolase was incubated at 37° C. (total volume=10 mL) for two days. The reaction was monitored by TLC (PrOH/water=7:3 v/v).

The title product was isolated by anion exchange chromatography on Dowex® 1×8–100 (HCOO⁻ form; 30×2 cm) using a gradient of formic acid (0.2M) as eluant. Fractions containing the product were pooled and freeze-dried. Yield 200 mg (80 percent).

$^1$H-NMR (500 MHz, D$_2$O) δ1.08 (d, $J_{8,CH3}$=6.5 CH$_3$), 1.62 (dd, $J_{3ax,3eq}$=13.3 Hz, $J_{3ax,4}$=11.5 Hz, H$_{3ax}$) 2.06 (dd, $J_{3eq,4}$=6.7 Hz, H$_{3eq}$), 3.39 (t, $J_{4,5}$=J$_{5,6}$=9.5 Hz, H-5), 3.675 (dd, $J_{6,7}$=0.8 Hz, $J_{7,8}$=8.2 Hz, H-7), 3.66 (dd, H-8), 3.8 (dd, H-6), 3.76–3.83 (ddd, H-4). $^{13}$C-NMR (125 MHz, reference CH$_3$ CN 1.6), 175.3800 (C-1), 96.1195 (C-2), 72.7438 (C-8), 72.3426 (C-6), 70.9565 (C-5), 69.3967 (C-7), 67.4548 (C-4), 39.3253 (C-3), 19.8777 (CH$_3$); [a]$_D^{20}$+60° (c 1.2, water); HRMS for C$_9$H$_{15}$O$_8$ calcd. 253.0923, found 253.0923.

B. Synthesis of 3-Deoxy-L-glycero-L-galactononulosonic acid (L-KDN) (Compound of Formula II)

A 0.1 M solution of L-mannose (1 mmol) in a 0.05 M potassium phosphate buffer, pH 7.2, containing 0.01 M dithiothreitol, sodium pyruvate (3 equivalent) and 10 U of NeuAc aldolase was incubated at 37° C. (total volume=10 mL) for two days. The reaction was monitored by TLC (PrOH/water=7:3 v/v).

The title product was isolated by anion exchange chromatography on Dowex® 1×8×100(HCOO⁻ form; 30×2 cm) using a gradient of formic acid (0.2M) as eluant. Fractions containing the product were pooled and freeze-dried. Yield 200 mg (80 percent).

The physical data ($^1$H, $^{13}$C-NMR and HRMS) were identical to the reported values of D-KDN except for the specific rotation [[α]$_D^{20}$-60° (c 1.2, H$_2$O)].

C. Synthesis of Compounds of Formulae III-IX

The compounds of Formulae III-IX were synthesized in accordance with the procedures of A and B, above. 3.86 (1H, qd, $J_{8-7}$=J$_{8-9}$=6.5 Hz, H-8), 3.32 (1H, dd, $J_{7-8}$=6.5 Hz, $J_{7-6}$=3.0 Hz, H-7), 2.06 (1H, ddd, $J_{3eq-3ax}$=12.0 Hz, J$_3$eq-4= 5.0 Hz, $J_{3eq-5}$=2.0 Hz, H-3eq), 1.85 (1H, dt, $J_{5eq-5ax}$=12.0 Hz, $J_{5eq-6}$=J$_{5eq-4}$=2.5 Hz, H-5eq), 1.53 (1H, q, $J_{5ax-4}$=J$_{5ax-5}$=J$_{5ax-5eq}$12.0 Hz, H$_{5ax}$), 1.51 (1H, t, $J_{3ax-3eq}$=J$_{3ax-4}$=12.0 Hz, H-3ax), 1.18 (d, $J_{9-8}$=6.5 Hz, H-9). $^{13}$C NMR (D$_2$O+ CD$_3$CN) 177.8 97.3, 77.2, 69.3, 67.5, 64.6 40.3, 35.8, 18.6. HRMS (FAB) calcd for C$_9$H$_{16}$O$_7$Na (M+Na$^+$) 259.0794, found 259.0799.

4. 5-Acetamido-3,5-dideoxy-L-glycero-β-L-galacto-2-nonulosonic acid (N-Acetyl-L-neuraminic acid) (Compound of Formula VII)

[a]$^{25}_D$+27.6° (c 0.17, H$_2$O [(lit.$^9$ for d-NeuAc: [a]$^{21}_D$−29° (H$_2$O)]; $^1$H NMR (D$_2$O) δ4.03 (1H, ddd, $J_{4-3ax}$=12.0 Hz, $J_{4-5}$=10.0 Hz, $J_{4-3eq}$=5.5 Hz, H-4), 4.01 (1H, dd, $J_{6-5}$=10.0 Hz, $J_{6-7}$=1.0 Hz, H-6), 3.90 (1H, t, $J_{5-6}$=J$_{5-4}$=10.0 Hz, H-5), 3.82 (1H, dd, $J_{9a-9b}$=12.0 Hz, $J_{9a-8}$=2.5 Hz, H-9a), 3.73 (1H, ddd, $J_{8-7}$=9.0 Hz, $J_{8-9b}$=6.0 Hz, $J_{8-9a}$=2.5 Hz, H$_8$), 3.60 (1H, dd, $J_{9b-9a}$=12.0 Hz, $J_{9b-8}$=6.0 Hz, H-9b), 3.51 (1H, dd, $J_{7-8}$=9.0 Hz, $J_{7-6}$=1.0 Hz, H-7), 2.26 (1H, dd, $J_{3eq-3ax}$=12.0 Hz, $J_{3eq-4}$=5.5 Hz, H-3eq), 2.03 (3H, s, acetyl), 1.84 (1H, t, $J_{3ax-3eq}$=J$_{3ax-4}$=12.0 Hz, H-3ax). $^{13}$C NMR (D$_2$O+CD$_3$CN) δ175.3 174.1, 95.9, 70.8, 70.6, 68.7, 67.2, 63.6, 52.5, 39.4, 22.5. Its $^1$H and $^{13}$C NMR spectra were identical with those of an authentic D-NeuAc from Pfanstiehl Co. HRMS (FAB) calcd for C$_{11}$H$_{18}$NO$_9$Na (M+Na$^+$) 331.2572, found 331.2579.

5. 3-Deoxy-L-manno-octulosonic Acid (L-KDO) (Compound of Formula IX)

The specific rotation and spectral data were obtained after L-KDO had been converted to its ammonium salt: [α]$^{25}_D$−37.2° (c 0.68, H$_2$O) [for D-KDO:[α]$^{27}_D$+42.3° (c 1.7, H$_2$O) Unger, *Adv. Charbohydr. Chem. Biochem.*, 381:323 (1981); authentic sample from Sigma [α]$^{25}_D$+40.1° (c 2.1, H$_2$O)]. Since KDO has an axial 5-OH group, it is known that it exists as a mixture of pyranose and furanose forms, and readily cyclizes to the corresponding lactone. The $^1$H and $^{13}$C NMR data of the predominant form are: $^1$H MMR (D$_2$O) δ4.03 (1H, ddd, $J_{4-3ax}$=13.0 Hz, $J_{4-3eq}$=5.5 Hz, $J_{4-5}$=3.0 Hz, H-4), 4.00 (1H, m, H-5) 3.87 (1H, dt, $J_{7-8b}$=3.0 Hz, $J_{7-6}$J$_{7-8a}$=5.5 Hz, H-7), 3.84 (1H, m, H-6), 3.78 (1H, dd, $J_{8b-8a}$=12.0 Hz, $J_{8b-7}$=3.0 Hz, H-8b), 3.60 (1H, dd, $J_{8a-8b}$=12.0 Hz, $J_{8a-7}$=5.5 Hz, H-8a), 2.00 (1H, t, $J_{3ax-3eq}$=J$_{3ax-4}$=13.0 Hz, H-3ax), 1.86 (1H, dd, $J_{3eq-3ax}$=13.0 Hz, $J_{3eq-4}$=5.5 Hz, H-3eq). $^{13}$C NMR (D$_2$O+CD$_3$CN) δ177.3, 96.8, 72.0, 71.3, 67.0, 66.6, 63.4, 34.0. $^1$H and $^{13}$C NMR spectra were identical with those of D-KDO from Sigma. HRMS (FAB) calcd for C$_8$H$_{14}$O$_8$Na(M+Na+) 261.0586, found 261.0591.

D. Benzyl 2-deoxy-β-D-glucopyranoside (Compound 1)

2-deoxy-D-glucose (Compound 1a, 2.5 g, 15.2 mmol) was dissolved in benzyl alcohol (20 mL), and then Dowex® 50W-X8 (H$^+$ form, 3.5 g) was added. The reaction solution was stirred at 60° C. for 24 hours. Then the resin was filtered off, and the product was purified by flash column chromatography with CHCl$_3$—MeOH (15:1) to give Compound 1 (2.67 g, 10.5 mmol) in 69 percent yield.

$^1$H NMR (CD$_3$OD) δ7.33 (5H, m), 4.98 (1H, br d, J$_{1-2ax}$=3.5 Hz, H-1), 4.70 (1H, d, J=12.0 Hz, benzyl), 4.46 (1H, d, J=12.0 Hz, benzyl), 3.88 (1H, ddd, J$_{3-2ax}$=12.0 Hz, J$_{3-4}$=9.5 Hz, J$_{3-2eq}$=5.0 Hz, H-3), 3.78 (1H, dd, J$_{6a-6b}$=12.0 Hz, J$_{6a-5}$=2.5 Hz, H-6a), 3.59 (1H, ddd, J$_{5-4}$=9.5 Hz, J$_{5-6b}$=6.0 Hz, J$_{5-6a}$=2.5 Hz, H-5), 3.58 (1H, dd, J$_{6b-6a}$=12.0 Hz, J$_{6b-5}$=6.0 Hz, H-6b), 3.25 (1H, t, J$_{4-3}$=J$_{4-5}$=9.5 Hz, H-4), 2.09 (1H, dd, J$_{2eq-2ax}$=13.0 Hz, J$_{2eq-3}$=5.0 Hz, H-2eq), 1.63 (1H, ddd, J$_{2ax-2eq}$=13.0 Hz, J$_{2ax-3}$=12.0 Hz, J$_{2ax-1}$=3.5 Hz, H-2ax). $^{13}$C NMR (CD$_3$OD) δ139.4, 129.3, 129.0, 138.6, 97.9, 74.3, 73.1, 69.9, 69.7, 62.8, 38.8. HRMS (FAB) calcd for C$_{13}$H$_{18}$O$_5$Na (M+Na$^+$) 277.1052, found 277.1041.

E. Benzyl 6-bromo-2,6-dideoxy-β-D-glucopyranoside (Compound 2)

A solution of triphenylphosphine (4.5 g, 17.3 mmol, 2.2 eq) in pyridine (30 mL) was added dropwise to a cooled solution of Compound 1 (2.0 g, 7.9 mmol) and CBr$_4$ (3.1 g, 9.4 mmol) in pyridine (30 mL) at zero degrees C. The mixture was then heated at 50° C. for 10 hours. After cooling, methanol (5 mL) was added dropwise, and the mixture was concentrated. The product was purified by flash column chromatography with CHCl$_3$—MeOH (32:1) to give 1.82 g (yield 73 percent) of Compound 2.

$^1$H NMR (CD$_3$OD): 7.20 (5H, m), 4.87 (1H, br d, J$_{1-2ax}$=3.5 Hz, H-1), 4.63 (1H, d, J=12.0 Hz, benzyl), 4.38 (1H, d, J=12.0 Hz, benzyl), 3.77 (1H, ddd, J$_{3-2ax}$=11.5 Hz, J$_{3-4}$=9.0 Hz, J$_{3-2eq}$=5.0 Hz, H-3), 3.67 (1H, dd, J$_{6a-6b}$=10.5 Hz, J$_{6a-5}$=2.0 Hz, H-6a), 3.64 (1H, ddd, J$_{5-4}$=9.0 Hz, J$_{5-6b}$=6.5 Hz, J$_{5-6a}$=2.0 Hz, H-5), 3.46 (1H, dd, J$_{6b-6a}$=10.5 Hz, J$_{6b-5}$=6.5 Hz, H-6b), 3.13 (1H, t, J$_{4-3}$=J$_{4-5}$=9.0 Hz, H-4), 2.01 (1H, dd, J$_{2eq-2ax}$=13.0 Hz, J$_{2ax-3}$=5.0 Hz, H-2eq), 1.55 (1H, ddd, J$_{2ax-2eq}$=13.0 Hz, J$_{2ax-3}$=11.5 Hz, J$_2$ax-1=3.5 Hz, H-2ax). $^{13}$C NMR (CD$_3$OD) δ139.0, 129.3, 129.1, 128.7, 97.7, 75.3, 73.1, 69.8, 69.7, 38.7, 34.6. HRMS (FAB) calcd for C$_{13}$H$_{17}$O$_4$NaBr (M+Na$^+$) 339.0208, found 339.0218.

F. Benzyl 2,6-dideoxy-β-D-glucopyranoside (Compound 3)

A solution of Bu$_3$SnH (1.0 g, 3.6 mmol, 1 mL) in toluene (10 mL) was added dropwise to a gentle refluxing solution of Compound 2 (0.76 g, 2.40 mmol) in toluene (15 mL) over 10 minutes, and then the mixture was refluxed for 10 hours. After cooling, the mixture was concentrated, and the residue was chromatographed on a flash column with CHCl$_3$—MeOH (29:1) to give crude Compound 3 which was acetylated with Ac$_2$O (10 mL), pyridine (10 mL) and catalytic amount of N,N-dimethylaminopyridine (DMAP). The product was purified by flash column chromatography with toluene-EtOAc (15:1) to give the corresponding peracetate, which was treated with NaOMe (2 mL, 1N solution) in MeOH (20 mL) for 0.5 hours at room temperature. The mixture was neutralized by adding Dowex® 50W-X8[H$^+$], then the resin was filtered off, and the filtrate was concentrated to give Compound 3.

$^1$H NMR (CDCl$_3$) δ7.28 (5H, m), 4.89 (1H, br d, J$_{1-2ax}$=3.5 Hz, H-1), 4.62 (1H, d, J=12.0 Hz, benzyl), 4.43 (1H, d, J=12.0 Hz, benzyl), 3.83 (1H, ddd, J$_{3-2ax}$=11.5 Hz, J$_{3-4}$=9.0 Hz, J$_{3-2eq}$=5.0 Hz, H-3), 3.64 (1H, dq, J$_{5-4}$=9.0 Hz, J$_{5-6}$=6.0 Hz, H-5), 2.97 (1H, t, J$_{4-3}$=J$_{4-5}$=9.0 Hz, H-4), 2.09 (1H, dd, J$_{2e-2ax}$=13.0 Hz, J$_{2eq-3}$=5.0 Hz, H-2eq), 1.63 (1H, ddd, J$_{2ax-2eq}$=13.0 Hz, J$_{2ax-3}$=11.5 Hz, J$_{2ax-1}$=3.5 Hz, H-2ax), 1.25 (3H, d, J$_{6-5}$=6.0 Hz, 6-CH$_3$). $^{13}$C NMR (CDCl$_3$) δ137.6, 128.4, 127.9, 127.7, 96.5, 77.9, 69.1, 68.8, 67.8, 37.7, 17.8. HRMS (FAB) calcd for C$_{13}$H$_{18}$O$_4$Na (M+Na$^+$) 261.1103, found 261.1116.

G. 2,6-Dideoxy-D-plucopyranose (Compound 4)

A solution of Compound 3 (0.56 g, 2.3 mmol) in 60 percent aqueous acetic acid (AcOH) (25 mL) was hydrogenated over 100 mg of 10 percent palladium on charcoal under atmospheric pressure. After 12 hours, the solution was filtered and the filtrate was concentrated in vacuo. By flash column chromatography with CHCl$_1$—MeOH (10:1), 0.29 g (2.0 mmol) of Compound 4 was obtained (85 percent yield).

β-isomer: $^1$H NMR (CD$_3$OD) δ5.12 (1H, br d, J$_{1-2ax}$3.5 Hz, H-1), 3.75 (1H, ddd, J$_{3-2ax}$=12.0 Hz, J$_{3-4}$=9.0 Hz, J$_{3-2}$=5.0 Hz, H-3), 3.18 (1H, dq, J$_{5-4}$=9.0 Hz, J$_{5-6}$=6.5 Hz, H-5), 2.85 (1H, t, J$_{4-3}$=J$_{4-5}$=9.0 Hz, H-4), 1.96 (1H, dd, J$_{2eq-2ax}$=13.0 Hz, J$_{2eq-3}$=5.0 Hz, H-2eq), 1.50 (1H, ddd, J$_{2ax-2eq}$=13.0 Hz, J$_{2ax-3}$=12.0 Hz, J$_{2ax-1}$=3.5 Hz, H-2ax), 1.14 (3H, d, J$_{6-5}$=6.5 Hz, 6-CH$_3$). $^{13}$C NMR (CD$_3$OD) δ92.6, 79.2, 73.2, 68.7, 39.8, 18.3. HRMS (FAB) calcd for C$_6$H$_{12}$O$_4$Na (M+Na$^+$) 171.0633, found 171.0640.

H. 2-Deoxy-L-alucopyranose (Compound 5)

A solution of triacetyl L-glucal (Compound 5a, 1.0 g, 3.7 mmol) and NaOMe (2 mL, 1N solution) in MeOH (15 mL) was stirred for 0.5 hours at room temperature. After the mixture was neutralized by adding Dowex® 50W-X8[H$^+$], the resin was filtered off, and the filtrate was concentrated.

The crude product was dissolved in a diluted H$_2$SO$_4$ solution (pH 1). After 24 hours, the reaction solution was neutralized with 1N NaOH, and then freeze-dried. The product was purified by flash column chromatography with CHCl$_3$—MeOH (5:1) to give Compound 5 (0.39 g, overall yield for these two steps: 65 percent).

$^1$H NMR (CD$_3$OD) for the a-isomer: δ4.78 (1H, dd, J$_{1-2ax}$=10.0 Hz, J$_{1-2eq}$=2.0 Hz, H-1), 3.85 (1H, dd, J$_{6a-6b}$=12.5 Hz, J$_{6a-5}$=2.0 Hz, H-6a), 3.67 (1H, dd, J$_{6b-6a}$=12.5 Hz, J$_{6b-5}$=6.0 Hz, H-6b), 3.54 (1H, ddd, J$_{3-2ax}$=12.0 Hz, J$_{3-4}$=9.0 Hz, J$_{3-2eq}$=5.0 Hz, H-3), 3.22 (1H, ddd, J$_{5-4}$=9.0 Hz, J$_{5-6b}$=6.0 Hz, J$_{5-6a}$=2.0 Hz, H-5), 3.15 (1H, t, J$_{4-3}$=J$_{4-5}$=9.0 Hz, H-4), 2.13 (1H, dd, J$_{2eq-2ax}$=12.5 Hz, J$_{2eq-3}$=5.0 Hz, J$_{2eq-1}$=2.0 Hz, H-2eq), 1.46 (1H, ddd, J$_{2ax-2eq}$=12.5 Hz, J$_{2ax-3}$=12.0 Hz, J$_{2ax-1}$=10.0 Hz, H-2ax). $^{13}$C NMR (CD$_3$OD) δ95.1, 78.1, 73.0, 72.6, 63.0, 41.8. HRMS (FAB) calcd for C$_6$H$_{12}$O$_5$Na (M+Na$^+$) 187.0582, found 187.0582.

I. 2,6-Dideoxy-L-glucopyrannose (2-deoxy-L-Rhamnose; Compound 6)

The reaction procedure was similar to that described above (from Compound 5a to Compound 5). The final product was purified by flash column chromatography with CHCl$_3$—MeOH (9:1) to give Compound 6 in 67 percent overall yield from triacetyl L-rhamnal, Compound 6a.

The data of $^1$H and $^{13}$C NMR are identical with those of Compound 4, which is an enantiomer of Compound 6. HRMS (FAB) calcd for C$_6$H$_{12}$O$_4$Na (M+Na$^+$) 171.0633, found 171.0640.

J. 2-Azido-2-deoxy-3,4,6-O-triacetyl-β-L-mannopyranosvl nitrate (Compound 7)

A solution of Compound 5a (1.50 g, 5.5 mmol) in CH$_3$CN (30 mL) was added dropwise to a solid mixture of NaN$_3$ (0.54 g, 8.3 mmol, 1.5 eq) and ammonium cerium nitrate (CAN, 9.1 g, 16.5 mmol, 3 eq) at about −20° C. The suspension was stirred vigorously under N$_2$. After seven hours, the starting material disappeared on TLC, the solution was poured into ice-water, and extracted with EtOAc. The combined extracts were successively washed with water, brine, dried over anhydrous MgSO$_4$ and concentrated in vacuo. The compound was chromatographed on a flash silica gel column with EtOAc-toluene (1:12) to give 1.57 g of the azido compound. From $^1$H NMR spectrum, three isomers were observed, (gluco and manno types which contained their α, β isomers). The major manno-type product was characterized:

$^1$H NMR (CDCl$_3$) δ6.22 (1H, d, J$_{1-2}$=2.0 Hz, H-1), 5.40 (1H, t, J$_{4-5}$=J$_{4-3}$=9.5 Hz, H-4), 5.25 (1H, dd, J$_{3-4}$=9.5 Hz, J$_{3-2}$=4.0 Hz, H-3), 4.28 (1H, dd, J$_{6a-6b}$=13.0 Hz, J$_{6a-5}$=5.0 Hz, H-6a), 4.21 (1H, dd, J$_{2-3}$=4.0 Hz, J$_{2-1}$=2.0 Hz H-2), 4.11 (1H, ddd, J$_{5-4}$=9.5 Hz, J$_{5-6a}$=5.0 Hz, J$_{5-6b}$=2.5 Hz, H-5), 4.11 (1H, dd, J$_{6b-6a}$=13.0 Hz, J$_{6b-5}$2.5 Hz, H-6b), 2.12 (3H, s, acetyl), 2.09 (3H, s, acetyl), 2.07 (3H, s, acetyl). $^{13}$C NMR (CDCl$_3$) δ170.4, 169.6, 169.2, 97.0, 71.0, 70.2, 64.6, 61.2, 58.6, 20.4, 20.3, 20.2. HRMS (FAB) calcd for C$_{12}$H$_{16}$N$_4$O$_{10}$Na (M+Na$^+$) 399.0674, found 399.0670.

K. 2-Azido-2-deoxy-1,3,4,6-tetra-O-acetyl-β-L-glucopyranose (Compound 8) and 2-Azido-2-deoxy-1,3,4,6-tetra-O-acetyl-β-L-mannopyranose (Compound 9)

The mixture mentioned above was used subsequently without further purification. Two equivalents of NaOAc (0.60 g, 7.3 mmol) were added to a solution of Compound 7 (1.37 g, 3.6 mmol) in acetic acid (30 mL), and the reaction was heated at 100° C. overnight (about 18 hours). After cooling, the reaction mixture was diluted with EtOAc (30 mL), then successively washed with water, aqueous NaHCO$_3$, brine, dried over anhydrous MgSO$_4$ and concentrated. The residue was chromatographed on a flash column with EtOAc-toluene (1:5) to give two products. The less polar isomer was identified as gluco-type Compound 8 (0.78 g), and the more polar isomer was identified as manno-type Compound 9 (0.75 g).

Compound 8: $^1$H NMR (CDCl$_3$) δ6.30 (1H, d, J$_{1-2}$=3.5 Hz, H-1), 5.46 (1H, t, J$_{3-2}$=J$_{3-4}$=10.0 Hz, H-3), 5.12 (1H, t, J$_{4-5}$=J$_{4-3}$=10.0 Hz, H-4), 4.30 (1H, dd, J$_{6a-6b}$=12.5 Hz, J$_{6a-5}$=4.0 Hz, H-6a), 4.08 (1H, ddd, J$_{5-4}$=10.0 Hz, J$_{5-6a}$=4.0 Hz, J$_{5-6b}$=2.5 Hz, H-5), 4.06 (1H, dd, J$_{6-6a}$=12.5 Hz, J$_{6b-5}$= 2.5 Hz, H-6b), 3.68 (1H, dd, J$_{2-3}$=10.0 Hz, J$_{2-1}$=3.5 Hz, H-2), 2.20 (3H, s, acetyl), 2.11 (3H, s, acetyl), 2.08 (3H, s, acetyl), 2.05 (3H, s, acetyl). $^{13}$C NMR (CDCl$_3$) δ170.4, 170.0, 169.4, 168.4, 89.8, 70.6, 69.6, 67.6, 61.3, 60.2, 20.8, 20.6, 20.6, 20.4. HRMS (FAB) calcd for C$_{14}$H$_{19}$N$_3$O$_9$ (M+Na$^+$) 396.1019, found 396.1023.

The manno-type isomer Compound 9 was further purified by recrystallization (prisms from diethyl ether): mp 130–131° ° C., [a]$^{25}$$_D$–82.1° (c 1.12, CHCl$_3$); $^1$H NMR (CDCl$_3$) δ6.11 (1H, d, J$_{1-2}$=2.0 Hz, H-1), 5.39 (1H, t, J$_{4-5}$=J$_{4-3}$=9.5 Hz, H-4), 5.36 (1H, dd, J$_{3-4}$=9.5 Hz, J$_{3-2}$=3.0 Hz, H-3), 4.24 (1H, dd, J$_{6a-6b}$=12.5 Hz, J$_{6a-5}$=4.5 Hz, H-6a), 4.07 (1H, dd, J$_{6b-6a}$=12.5 Hz, J$_{6b-5}$=2.5 Hz, H-6b), 4.03 (dd, J$_{2-3}$=3.0 Hz, J$_{2-1}$=2.0 Hz, H-2), 4.02 (1H, ddd, J$_{5-4}$=9.5 Hz, J$_{5-6a}$=4.5 Hz, J$_{5-6b}$=2.5 Hz, H-5), 2.16 (3H, s, acetyl), 2.11 (3H, s, acetyl), 2.09 (3H, s, acetyl), 2.05 (3H, s, acetyl). $^{13}$C NMR (CDCl$_3$) δ170.7, 170.0, 169.3, 168.2, 91.3, 70.7, 70.5, 65.2, 61.7, 60.4, 20.9, 20.7, 20.6, 20.5. HRMS (FAB) calcd for C$_{14}$H$_{19}$N$_3$O$_9$Na (M+Na$^+$) 396.1019, found 396.1023.

L. 2-Acetamido-2-deoxy-1,3,4,6-tetra-O-acetyl-β-L-mannopyranose (Compound 10)

A solution of Compound 9 (0.60 g, 1.62 mmol) in Ac$_2$O (20 mL) was hydrogenated over 70 mg of 10 percent palladium on charcoal under atmospheric pressure. After 10 hours, the solution was filtered and the filtrate was concentrated in vacuo. By flash column chromatography with EtOAc-toluene (2.5:1), 0.52 g of Compound 10 was obtained in 83 percent yield. $^1$H NMR (CDCl$_3$) δ6.03 (1H, d, J$_{1-2}$=1.5 Hz, H-1), 5.34 (1H, dd, J$_{3-4}$=10.0 Hz, J$_{3-2}$=5.0 Hz, H-3), 5.18 (1H, t, J$_{4-5}$=J$_{4-3}$=10.0 Hz, H-4), 4.65 (1H, ddd, J$_{5-4}$=10.0 Hz, J$_{5-6a}$=5.0 Hz, J$_{5-6b}$=2.0 Hz, H-5), 4.29 (1H, dd, J$_{6a-6b}$12.5 Hz, J$_{6a-5b}$=5 Hz, H-6a), 4.06 (1H, dd, J$_{2-3}$=5.0 Hz, J$_{2-1}$=1.5 Hz, H-2), 4.05 (1H, dd, J$_{6b-6a}$=12.5 Hz, J$_{6b-5}$=2.0 Hz, H-6b), 2.18 (3H, s, acetyl), 2.10 (3H, s, acetyl), 2.07 (3H, s, acetyl), 2.07 (3H, s, acetyl), 2.01 (3H, s, acetyl). $^{13}$C NMR (CDCl$_3$) δ170.4, 170.1, 170.0, 169.6, 168.0, 91.7, 73.4, 70.1, 65.5, 62.1, 49.3, 23.2, 20.8, 20.7, 20.7, 20.6. HRMS (FAB) calcd for C$_{16}$H$_{23}$NO$_{10}$Na (M+Na$^+$) 412.1220, found 412.1224.

M. 2-Acetamido-2-deoxy-β-L-mannopyranose (N-Acetyl-L-mannosamine) (Compound 11)

A solution of aqueous LiOH (0.3M, 20 mL) was added dropwise to a solution containing Compound 10 (0.52 g, 1.34 mmol) in THF-H$_2$O (3:1, 22 mL). From TLC, the reaction was complete within 30 minutes. Dowex® 50W-X8[H$^+$] was added to neutralize the solution, then the resin was filtered off, and the filtrate was concentrated. The product was purified by flash column chromatography with CHCl$_3$—MeOH (3.5:1) to obtain 0.29 g (1.3 mmol) of Compound 11 (97 percent yield). Further purification was carried out with Bio Gel P-2 chromatography using water as eluent.

$^1$H NMR (CD$_3$OD) for the major δ-isomer: δ4.95 (1H, d, J$_{1-2}$=1.5 Hz, H-1), 4.23 (1H, dd, J$_{2-3}$=4.5 Hz, J$_{2-1}$=1.5 Hz, H-2), 3.95 (1H, dd, J$_{3-4}$=10.0 Hz, J$_{3-2}$=4.5 Hz, H-3), 3.80 (3H, dd, J$_{6a-6b}$=12.0 Hz, J$_{6a-5}$=4.5 Hz, H-6a), 3.72 (1H, m, H-5), 3.72 (1H, dd, J$_{6b-6a}$=12.0 Hz, J$_{6b-5}$=2.0 Hz, H-6b), 3.55 (1H, t, J$_{4-5}$=J$_{4-3}$=10.0 Hz, H-4), 1.91 (3H, s, acetyl). $^{13}$C NMR (CD$_3$OD) δ174.0, 94.9, 73.4, 70.6, 68.4, 62.2, 55.1, 22.6. The $^1$H and $^{13}$C NMR spectra were identical with those of an authentic sample of the D-enaniomer from Sigma. HRMS (FAB) calcd for C$_8$H$_5$NO$_6$Na (M+Na$^+$) 244.0797, found 244.0797.

N. 2-Azido-2-deoxy-L-mannopyranose (Compound 9a)

A solution of Compound 9 (541 mg, 1.45 mmol) in 3N aqueous hydrochloric acid (100 mL) was warmed until solution became clear and then stirred at room temperature. After 10 hours, n-butanol was added and the solution was evaporated. The residue was chromatographed on a flash column with CHCl$_3$—MeOH (4:1) to give 0.244 g of Compound 9a in 82 percent yield.

[α]$^{25}$$_D$–13.60 (c 0.98, H$_2$O); $^1$H-NMR (CD$_3$OD) for the major β-isomer: δ4.90 (1H, d, J$_{1-2}$=1.5 Hz, H-1), 4.02 (1H, dd, J$_{3-4}$=9.5 Hz, J$_{3-2}$=4 Hz, H-3), 3.80 (1H, dd, J$_{2-3}$=4 Hz, J$_{2-1}$=1.5 Hz, H-2), 3.79 (1H, dd, J$_{6a-6b}$=12 Hz, J$_{6a-5}$=2 Hz, H-6a), 3.73 (1H, dd, J$_{5-4}$=9.5 Hz, J$_{5-6b}$=6 Hz, J$_{5-6a}$=2 Hz, H-5), 3.67 (1H, dd, J$_{6b-6a}$=12 Hz, J$_{6b-6}$=6 Hz H-6b), 3.58 (t, J$_{4-3}$=J$_{4-5}$=9.5 Hz, H-4). $^{13}$C-NMR (CD$_3$OD) δ93.8, 74.1, 72.2, 68.9, 66.6, 62.8. HRMS (FAB) calcd for C$_6$H$_{11}$N$_3$O$_5$Na 228.0596, found 228.0596.

EXAMPLE 2

Enzymatic Reactions

A 0.1M solution of sugar (1 mmol) in a 0.05M potassium phosphate buffer (pH 7.4) containing 11mM dithiothreitol, sodium pyruvate (10 eq), and 10 units of NeuAc aldolase was incubated at 37° C. (total volume=10 mL) for three days. The reaction was monitored by TLC (i-PrOH/H$_2$O =7:3 v/v). The product was isolated by anion exchange chromatography on Dowex® 1-X8 (HCO$_3$$^-$ form; 20×2.5 cm) using a gradient of ammonium bicarbonate (0→0.2M) as the eluant. Fractions containing the products were pooled and freeze-dried, deionized with Dowex® 50W-X8 [H$^+$] and again freeze-dried. Finally, Bio Gel P-2 chromatography was applied to obtain the pure compound.

EXAMPLE 3

Improved Enzymatic Preparation of N-Acetyl-D-neuraminic acid

A solution containing N-acetyl-D-mannosamine monohydrate (1.89 g, 7.5 mmol), sodium pyruvate (5.89 g, 52.5 mmol), NaN$_3$ (25 mg), phosphate buffer (0.1M, 2.5 mL, pH 7.5) and water (35 mL) was adjusted to pH 7.5. NeuAc aldolase (Shinko American, Inc., 10 U) was added and the mixture was stirred at 25° C. for two days. More enzyme (5 U) was added and the mixture was further stirred for additional two days until about 80 percent of ManNAc was consumed based on the $^1$H-NMR analysis [N-acetyl signals of ManNAc at δ2.04 and 2.08 (1:1, two anomers) in $D_2O$ and that of NeuAc at δ2.04]. The mixture was adjusted to pH 2.0 by addition of Dowexg 50W-X8 ($H^+$ form, 20–50 mesh) and incubated for one hour to denature the enzyme; the mixture was then adjusted to pH 6.5 by adding concentrated aqueous ammonia solution.

Baker's yeast was pre-treated separately as follows: Baker's yeast (Sigma type II, YSC-2, 15 g, $16/500 g) was suspended in cold water (200 mL) and the mixture was stirred at 4° C. overnight (about 18 hours). The cells were harvested at 10,000×g (8,500 r.p.m.) for 30 minutes at 4° C. and washed twice with cold water (100 mL). This procedure is absolutely necessary to remove all of the polar acidic materials prior to use.

The collected cells (35 mL) containing pyruvate decarboxylase were then resuspended in water (40 mL), then added to the aldol product solution obtained above. After antifoam AF emulsion (Dow-Corning-Nakaraitesque, diluted to a 10 percent aqueous solution, 0.4 mL) was added, the mixture was stirred with bubbling of air (1,000 mL/min). The pH was kept between 5.8–6.5 by occasional addition of Dowex® 50W-X8 ($H^+$ form, 20–50 mesh). The consumption of pyruvate was determined by lactate dehydrogenase assay for the remaining pyruvate. The NMR spectrum of the sample taken after six hours showed a complete decomposition of pyruvate (δ2.36 for $CH_3COCO_2^-$ and δ1.52 for $CH_3C(OH)_2CO_2$ in $D_2O$).

The yeast cells were removed by centrifugation at 10,000×g (8,500 r.p.m.) for 30 minutes at 4° C. and the cells were washed twice with water (100 mL). The pH value of the combined extract was adjusted to 2.3 by addition of Dowex® 50W-X8 ($H^+$ form) and the solution was concentrated in vacuo. The residue was suspended in 50 percent aqueous methanol (200 mL) and left to stand overnight (about 18 hours) at 4° C. The precipitated materials were removed by centrifugation at 10,000×g (8,500 r.p.m.) for 30 minutes at 4° C., and the residue was washed twice with 50 percent aqueous methanol (100 mL).

The solution was concentrated in vacuo and the residue was diluted with water (400 mL). The pH value was then adjusted to 5.5 by addition of concentrated aqueous ammonia solution. To this solution was added Dowex® 1-X8 ($HCO_2^+$ form, 20–50 mesh, 100 mL of the bed volume). After washing with water, the resin was eluted with 2M formic acid (400 mL). Concentration of the eluant afforded crystalline product, which was washed successively with methanol and diethyl ether to give pure NeuAc (987 mg, 3.2 mmol; 42.6 percent yield based on D-ManNAc), $[\alpha]_D^{25}$–34.0° (c 2.09, $H_2O$) [authentic NeuAc from Pfanstiehl Co., $[\alpha]_D^{20}$–32° (c 2.0, $H_2O$)]. The NMR spectrum in $D_2O$ was identical with that of authentic NeuAc. A similar result was obtained with the use of commercially available pyruvate decarboxylase (EC 4.1.1.1, Sigma P6810, $80/100 U) instead of yeast.

A larger scale synthesis was carried out starting from a mixture of N-acetyl-D-mannosamine (23.4 g) and N-acetyl-D-glucosamine (4.9 g), which was obtained by the base-catalyzed epimerization of N-acetyl-D-glucosamine [Simon et al., *J. Am. Chem. Soc.*, 110:7159 (1988)]. In this case, the decarboxylation procedure was slightly modified as follows: The pH value of the reaction mixture was adjusted to 6.0 by the addition of 2N NaOH solution after the denaturation of NeuAc aldolase. The subsequent procedure was the same as described above.

Finally, more than 10 g of NeuAc could be isolated simply by recrystallization, without any treatment of anion exchange resin. After the removal of precipitates by the treatment with 50 percent aqueous methanol, the concentrated residue was dissolved in 75 percent aqueous acetic acid (100 mL) and the solution was left to stand overnight (about 18 hours) at 4° C. The resulting thick suspension was diluted with cold 75 percent aqueous acetic acid (100 mL) and centrifuged at 10,000×g (8,500 rpm) for 30 minutes at 4° C. The precipitated NeuAc was washed successively with cold 75 percent aqueous acetic acid (100 mL) and cold methanol (100 mL) by the use of centrifugation. The precipitates were collected by filtration, and washed with cold methanol and diethyl ether to give 12.1 g of NeuAc. For a larger scale synthesis, the aldolase can be used in an immobilized form [Liu et al., *J. Am. Chem. Soc.*, 114:3901 (1991)].

EXAMPLE 4

Kinetic Measurements

The rates for aldolase-catalyzed reactions were obtained by measuring the amount of remaining pyruvate [Kim et al., *J. Am. Chem. Soc.*, 110:6481 (1988)]. The reactions were carried out in 0.1M phosphate buffer (pH 7.5) containing 0.4 U of the enzyme, varied concentrations of pyruvate (2.0, 2.5, 3.33, 5, and 10 mM), and varied concentrations of carbohydrates (0.2, 0.25, 0.33, and 0.50M) in 0.5 mL of solution. Each solution was incubated at 37° C. Periodically, a small volume (20–50 mL) was withdrawn and mixed with an assay solution (1.4 mL) containing 0.1M phosphate (pH 7.5), 0.3 mM NADH, and 20–30 U of L-lactate dehydrogenase. The decrease in absorbance at 340 nm was measured and the amount of the unreacted pyruvate was determined using $6220M^{-1}cm^{-1}$ as the molar absorbance of NADH. The kinetic parameters were obtained from the Lineweaver-Burk plots.

For the relative rate measurements, the concentration of pyruvate and sugar were fixed at 10 mM and 0.25M, respectively. Other conditions were the same as the above.

TABLE I

Relative Rates of Sialic Acid Aldolase-Catalyzed Reaction with Different Sugars

| Sugar | Rel rate[a] | Sugar | Rel rate |
|---|---|---|---|
| N-Acetyl-D-mannosamine | 100[b] | D-Talose | 16 |
| N-Acetyl-L-mannosamine | 0.8 | L-Talose | 1.0 |
| D-Mannose | 91 | D-Gulose | 3 |
| L-Mannose | 2.6 | L-Gulose | 20 |
| 2-Deoxy-D-glucose | 35 | D-Arabinose | 1.2 |
| 2-Deoxy-L-glucose | 1.0 | L-Arabinose | 1.6 |
| 2,6-Dideoxy-D-glucose | 18 | 2-Azido-2-deoxy-D-mannose | 13 |
| 2-Deoxy-L-rhamnose | 0.6 | 1-Azido-2-deoxy-L-mannose | 0.2 |

[a]Rel Rate = Relative Rate
[b]specific activity = 18 U/mg. 1 U = 1 μmol of NeuAc formed per minute.

TABLE II

| Kinetic parameters ($K_m$, $V_{max}$) for the Sialic Acid Aldolase-Catalyzed Reaction with D- and L-Mannose | | |
|---|---|---|
| substrate | $K_m$ (M) | $V_{max}$ (U/mg)[a] |
| D-Mannose | 2.5 | 43 |
| L-Mannose | 0.86 | 3 |

[a] 1 U = 1 μmol of product formed per minute.

The foregoing is intended as illustrative of the present invention but not limiting. Numerous variations and modifications may be effected without departing from the true spirit and scope of the novel concepts of the invention.

We claim:

1. A compound of the Formula V:

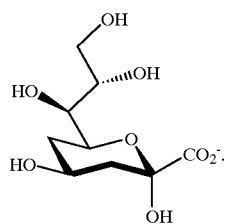

V

2. A compound of the Formula VI:

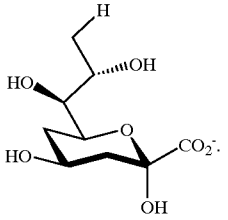

VI

3. A compound of the Formula VII:

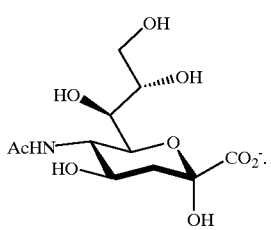

VII

4. A compound of the Formula VIII:

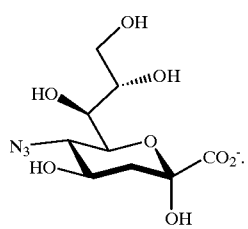

VIII

5. A process of synthesizing a compound of the Formula V, VI, VII or VIII, below:

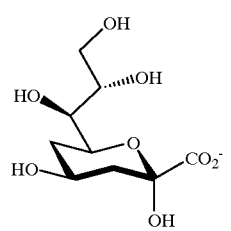

V

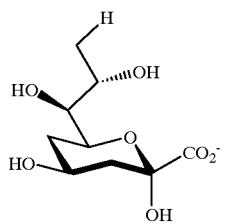

VI

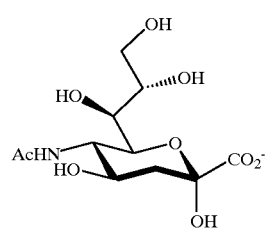

VII

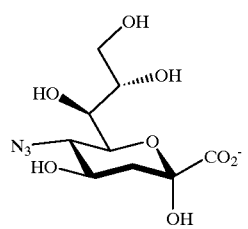

VIII comprising the steps of:
(a) admixing in an aqueous solvent pyruvate, in the presence of a catalytic amount of sialic acid aldolase, with an acceptor substrate 2-deoxy-L-glucose, 2-deoxy-L-rhamnose, N-acetyl-L-mannosamine or 2-azido-2-deoxy-L-mannose, respectively, to form a reaction mixture; and
(b) maintaining said reaction mixture for a time period and under biological reaction conditions sufficient for condensation of said pyruvate with said acceptor substrate and formation of a compound of Formula V, VI, VII or VIII.

6. The process according to claim 5 further comprising recovering the formed compound of Formula V, VI, VII or VIII.

7. A process for synthesizing a ketoaldonic acid that comprises (a) admixing in an acrueous solvent (i) an excess of pyruvate, (ii) sialic acid aldolase and (iii) an acceptor substrate aldose for said aldolase to form a reaction mixture;

(b) maintaining said reaction mixture for a time period and under biological reaction conditions sufficient for the condensation of said pyruvate and said acceptor substrate aldose to form a ketoaldonic acid in the reaction mixture;

(c) admixing a catalytic amount of pyruvate decarboxylate into the reaction mixture to form a further admixture;

(d) maintaining said further admixture for a time period and under biological reaction conditions sufficient for the excess pyruvate to decompose; and e) recovering the formed ketoaldonic acid.

8. The process according to claim 7 wherein said sialic acid aldolase is denatured prior to the admixture of said pyruvate decarboxylase.

9. The process according to claim 7 wherein said pyruvate decarboxylase is provided by the culturing of acid-free baker's yeast in said reaction mixture.

10. A compound of the Formula IX:

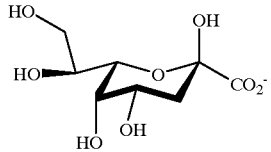

IX

* * * * *